US008337551B2

(12) United States Patent
Linhardt et al.

(10) Patent No.: US 8,337,551 B2
(45) Date of Patent: *Dec. 25, 2012

(54) BIOMEDICAL DEVICES

(75) Inventors: Jeffrey G. Linhardt, Fairport, NY (US); Ivan M. Nunez, Penfield, NY (US); Joseph A. McGee, Canandaigua, NY (US); Jennifer Hunt, Batavia, NY (US); Michele Alton, Rochester, NY (US); Drazen Pavlovic, Zagreb (HR); Devon A. Shipp, Potsdam, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/226,691

(22) Filed: Sep. 7, 2011

(65) Prior Publication Data

US 2012/0022180 A1 Jan. 26, 2012

Related U.S. Application Data

(63) Continuation of application No. 12/456,419, filed on Jun. 16, 2009, now Pat. No. 8,043,369.

(51) Int. Cl.
*A61F 2/14* (2006.01)
*A61F 2/16* (2006.01)
*C08G 77/22* (2006.01)

(52) U.S. Cl. ............... 623/5.11; 623/6.11; 623/6.56; 528/30

(58) Field of Classification Search ............ 623/5.11, 623/6.11, 6.56
See application file for complete search history.

(56) References Cited

U.S. PATENT DOCUMENTS

| | | | |
|---|---|---|---|
| 3,408,429 A | 10/1968 | Wichterle | |
| 3,660,545 A | 5/1972 | Wichterle | |
| 4,113,224 A | 9/1978 | Clark et al. | |
| 4,136,250 A | 1/1979 | Mueller et al. | |
| 4,153,641 A | 5/1979 | Deicherte et al. | |
| 4,197,266 A | 4/1980 | Clark et al. | |
| 4,327,203 A | 4/1982 | Deichert et al. | |
| 4,355,147 A | 10/1982 | Deichert et al. | |
| 4,555,732 A | 11/1985 | Tuhro | |
| 4,740,533 A | 4/1988 | Su et al. | |
| 4,910,277 A | 3/1990 | Bambury et al. | |
| 4,954,587 A | 9/1990 | Mueller | |
| 5,010,141 A | 4/1991 | Mueller | |
| 5,034,461 A | 7/1991 | Lai et al. | |
| 5,070,215 A | 12/1991 | Bambury et al. | |
| 5,079,319 A | 1/1992 | Mueller | |
| 5,260,000 A | 11/1993 | Wandu et al. | |
| 5,270,418 A | 12/1993 | Kunzler et al. | |
| 5,271,875 A | 12/1993 | Appleton et al. | |
| 5,310,779 A | 5/1994 | Lai | |
| 5,321,108 A | 6/1994 | Kunzler et al. | |
| 5,358,995 A | 10/1994 | Lai et al. | |
| 5,387,662 A | 2/1995 | Kunzler et al. | |
| 6,440,571 B1 | 8/2002 | Valint, Jr. et al. | |
| 6,867,245 B2 | 3/2005 | Iwata et al. | ............ 523/107 |
| 6,902,812 B2 | 6/2005 | Valint, Jr. et al. | |
| 7,473,740 B2 | 1/2009 | Zard et al. | ............ 525/329.4 |
| 2005/0203256 A1 | 9/2005 | Destarac et al. | ............ 525/337 |

FOREIGN PATENT DOCUMENTS

| | | |
|---|---|---|
| WO | WO 96/31792 | 10/1996 |
| WO | WO2008124093 A1 | 10/2008 |
| WO | WO2009117374 A1 | 9/2009 |

OTHER PUBLICATIONS

International Search Report (PCT/ISA/210) and Written Opinion (PCT/ISA/237) mailed on Sep. 28, 2010.
Pai, T S C et al. "Synthesis of Amphiphilic Block Copolymers based on poly(dimethylsiloxane) via fragmentation . . ." in J. Polymer, vol. 45, No. 13, Jun. 1, 2004, pp. 4383-4389.
Mayadunne R T A et al. "Living free radical polymerization with reverisble addition-fragmentation chain . . . " in Macromolecules, vol. 36, No. 5, Mar. 11, 2003, pp. 1505-1513.
Pavlovic, D et al. "Synthesis of amphiphilic multiblock and triblock copolymers of polydimethylsiloxane . . . " in J Polym. Sci., vol. 46, No. 21, Nov. 1, 2008, pp. 7033-7048.
Bernard, J et al. "Poly(vinyl ester) star polymers via xanthate-mediated living radical polymerization . . . " in Macromolecules, vol. 38, No. 13, Jun. 28, 2005, pp. 5475-5484.
Karunakaran R et al. "Synthesis, characterization, and crosslinking of methacrylate-telechelic . . . " in J. Polym Sci, Part A, vol. 45, No. 18, Sep. 15, 2007, pp. 4284-4290.
Lai, Yu-Chin, "The Role of Bulky Polysiloxanylalkyl Methacrylates in Polyurethane-Polysiloxane Hydrogels," Journal of Applied Polymer Science, vol. 60, 1193-1199 (1996).
Karunakaran et al., "Synthesis, Characterization, and Crosslinking of Methacrylate-Telechelic PDMAAm-b-PDMS-b-PDMAAm Copolymers", Journal of Polymer Science: Part A: Polymer Chemistry, vol. 45, pp. 4284-4290 (2007).

*Primary Examiner* — Robert S Loewe
(74) *Attorney, Agent, or Firm* — Glenn D. Smith

(57) ABSTRACT

Biomedical devices such as silicone hydrogels formed from a polymerization product of a mixture comprising (a) a siloxane-containing homopolymer which has only one thio carbonyl thio fragment of a reversible addition fragmentation chain transfer (RAFT) agent; and (b) one or more biomedical device-forming comonomers are disclosed.

17 Claims, No Drawings

BIOMEDICAL DEVICES

PRIOR APPLICATIONS

This application is a continuation of application Ser. No. 12/456,419, filed Jun. 16, 2009.

BACKGROUND OF THE INVENTION

1. Technical Field

The present invention generally relates to biomedical devices such as ophthalmic lenses

2. Description of Related Art

Biomedical devices such as ophthalmic lenses made from siloxy-containing materials have been investigated for a number of years. Such materials can generally be sub-divided into two major classes, namely hydrogels and non-hydrogels. Hydrogels can absorb and retain water in an equilibrium state whereas non-hydrogels do not absorb appreciable amounts of water. Regardless of their water content, both hydrogels and non-hydrogels tend to have relatively hydrophobic, non-wettable surfaces.

Hydrogels represent a desirable class of materials for many biomedical applications, including contact lenses and intraocular lenses. Hydrogels are hydrated, crosslinked polymeric systems that contain water in an equilibrium state. Silicone hydrogels are a known class of hydrogels and are characterized by the inclusion of a silicone-containing monomer. Silicone hydrogels have typically been prepared by polymerizing mixtures containing at least one silicone-containing monomer and at least one hydrophilic monomer. Either the silicone-containing monomer or the hydrophilic monomer function as a crosslinking agent (a crosslinker being defined as a monomer having multiple polymerizable functionalities) or a separate crosslinker may be employed.

In the field of biomedical devices such as contact lenses, various physical and chemical properties such as, for example, oxygen permeability, wettability, material strength and stability are but a few of the factors that must be carefully balanced in order to provide a useable contact lens. For example, since the cornea receives its oxygen supply from contact with the atmosphere, good oxygen permeability is an important characteristic for certain contact lens material. Wettability also is important in that, if the lens is not sufficiently wettable, it does not remain lubricated and therefore cannot be worn comfortably in the eye. Accordingly, the optimum contact lens would have at least both excellent oxygen permeability and excellent tear fluid wettability.

An advantage of silicone hydrogels over non-silicone hydrogels is that the silicone hydrogels typically have higher oxygen permeability due to the inclusion of the siloxy-containing monomer. Silicone-containing monomers for use in the formation of silicone hydrogels are well known and numerous examples are disclosed in, for example, U.S. Pat. Nos. 4,136,250; 4,153,641; 4,740,533; 5,034,461; 5,070,215; 5,260,000; 5,310,779 and 5,358,995. However, one problem associated with silicone lenses is the surfacing of silicone chains which create hydrophobic areas on the lens. This will adversely impact wettability, on eye-movement and comfort to the user.

Karunakaran et al., "Synthesis, Characterization, and Crosslinking of Methacrylate-Telechelic PDMAAm-b-PDMS-b-PDMAAm Copolymers", Journal of Polymer Science: Part A: Polymer Chemistry, Vol. 45, pp. 4284-4290 (2007) ("Karunakaran et al.") discloses the preparation of a new amphiphilic methacrylate-telechelic pentablock copolymer by reversible addition fragmentation chain transfer ("RAFT") polymerization. As shown in Scheme I in Karunakaran et al., a polysiloxane monomer comprising one or more thio carbonyl fragments of a RAFT agent (2) is used as an intermediate in the preparation of the amphiphilic methacrylate-telechelic pentablock copolymer. Karunakaran et al. further discloses that the new amphiphilic methacrylate-telechelic pentablock copolymers can be used in an ophthalmic application such as in the formation of a contact lens. However, the process for making the amphiphilic methacrylate-telechelic pentablock copolymers is time consuming and employs different reagents and process conditions. This, in turn, can cause reproducibility problems. In addition, the methacrylate-telechelic copolymers prepared by Karunakaran et al. are cross-linking agents, which can increase the "effective" cross-link density of the resulting product resulting in a higher modulus of the product.

Accordingly, there remains a need to provide improved silicone hydrogels that are soft enough to make soft contact lenses, which possess high oxygen permeability, suitable water content, and sufficient elasticity, and are comfortable to the contact lens wearer. It would also be desirable to provide improved silicone hydrogels that are easy to manufacture in a simple, cost effective manner.

SUMMARY OF THE INVENTION

In accordance with one embodiment of the present invention, a biomedical device is provided comprising a polymerization product of a mixture comprising (a) a siloxane-containing homopolymer comprising one or more thio carbonyl thio fragments of a reversible addition fragmentation chain transfer ("RAFT") agent; and (b) one or more biomedical device-forming monomers.

In accordance with a second embodiment of the present invention, a soft contact lens is provided comprising a polymerization product of a mixture comprising (a) a siloxane-containing homopolymer comprising one or more thio carbonyl thio fragments of a RAFT agent; and (b) one or more soft contact lens-forming monomers.

In accordance with a third embodiment of the present invention, a silicone hydrogel is provided comprising a hydrated polymerization product of a mixture comprising (a) a siloxane-containing homopolymer comprising one or more thio carbonyl thio fragments of a RAFT agent; and (b) a hydrophilic monomer.

The biomedical devices of the present invention such as a silicone hydrogel are advantageously formed from a siloxane-containing homopolymer comprising one or more thio carbonyl thio fragments of a RAFT agent. Unlike Karunakaran et al., applicants have discovered that the siloxane-containing homopolymers comprising one or more thio carbonyl thio fragments of a RAFT agent disclosed herein are readily capable of being incorporated into a biomedical device-forming formulation to form biomedical devices which are believed to possess high oxygen permeability while having a lower modulus. This will provide a higher level of comfort to the wearer.

Also, unlike Karunakaran et al., the siloxane-containing homopolymers described herein can not form covalent cross-links in the resulting product, but rather extend the polymer chain after reaction with a suitable monomer. This will result in a product having a lower "effective" cross-link density and, therefore, a relatively low modulus. Thus, the siloxane-containing homopolymer RAFT agents can actively participate in free radical polymerization to covalently link the siloxane-containing homopolymer RAFT agents to the resulting network. In addition, the siloxane-containing homopolymers can be prepared in a simple, cost efficient manner prior to being incorporated into the biomedical device-forming formulation.

DETAILED DESCRIPTION OF THE PREFERRED EMBODIMENTS

The present invention is directed to biomedical devices intended for direct contact with body tissue or body fluid. As used herein, a "biomedical device" is any article that is designed to be used while either in or on mammalian tissues or fluid, and preferably in or on human tissue or fluids. Representative examples of biomedical devices include, but are not limited to, artificial ureters, diaphragms, intrauterine devices, heart valves, catheters, denture liners, prosthetic devices, ophthalmic lens applications, where the lens is intended for direct placement in or on the eye, such as, for example, intraocular devices and contact lenses. The preferred biomedical devices are ophthalmic devices.

As used herein, the term "ophthalmic device" refers to devices that reside in or on the eye. These devices can provide optical correction, wound care, drug delivery, diagnostic functionality or cosmetic enhancement or effect or a combination of these properties. Useful ophthalmic devices include, but are not limited to, ophthalmic lenses such as soft contact lenses, e.g., a soft, hydrogel lens, soft, non-hydrogel lens and the like, intraocular lenses, overlay lenses, ocular inserts, optical inserts and the like. As is understood by one skilled in the art, a lens is considered to be "soft" if it can be folded back upon itself without breaking. Preferred ophthalmic devices are soft contact lenses, and most preferred are soft contact lenses made from silicone hydrogels.

The biomedical devices of the present invention are formed from a polymerization product of a mixture comprising (a) a siloxane-containing homopolymer comprising one or more thio carbonyl thio fragments of a reversible addition fragmentation chain transfer ("RAFT") agent (or RAFT group); and (b) one or more biomedical device-forming monomers.

The thio carbonyl thio fragments in the siloxane-containing homopolymer are based upon thio carbonyl thio chemistry which is well known to those of ordinary skill in the art. The thio carbonyl thio fragment can be, for example, a xanthate-containing fragment, trithiocarbonate-containing fragment, dithiocarbamate-containing fragment, dithio ester-containing fragment, or a dithio or trithiocarboxylic acid fragment, wherein each fragment contains a thiocarbonyl group and preferably a thiocarbonyl thio group. One class of thio carbonyl thio fragments is of the general formula:

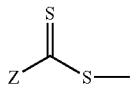

wherein Z is a substituted oxygen (e.g., xanthates (—O—R)), a substituted nitrogen (e.g., dithiocarbamates (—NRR)), a substituted sulfur (e.g., trithiocarbonates (—S—R)), a substituted or unsubstituted $C_1$-$C_{20}$ alkyl group, $C_3$-$C_{25}$ unsaturated, or partially or fully saturated ring or a carboxylic acid-containing group (e.g., dithioesters (—R)); and R is independently a straight or branched, substituted or unsubstituted $C_1$-$C_{30}$ alkyl group, a substituted or unsubstituted $C_3$-$C_{30}$ cycloalkyl group, a substituted or unsubstituted $C_3$-$C_{30}$ cycloalkylalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ arylalkyl group, $C_1$-$C_{20}$ carboxylic acid group, a $C_1$-$C_{20}$ ester group, an ether or polyether-containing group, an alkyl- or arylamide group, an alkyl- or arylamine group, a substituted or unsubstituted $C_5$-$C_{30}$ heteroaryl group, a substituted or unsubstituted $C_3$-$C_{30}$ heterocyclic ring, a substituted or unsubstituted $C_4$-$C_{30}$ heterocycloalkyl group, a substituted or unsubstituted $C_6$-$C_{30}$ heteroarylalkyl group, and combinations thereof.

Representative examples of alkyl groups for use herein include, by way of example, a straight or branched alkyl chain radical containing carbon and hydrogen atoms of from 1 to about 30 carbon atoms and preferably from 1 to about 12 carbon atoms with or without unsaturation, to the rest of the molecule, e.g., methyl, ethyl, n-propyl, 1-methylethyl (isopropyl), n-butyl, n-pentyl, methylene, ethylene, etc., and the like.

Representative examples of cycloalkyl groups for use herein include, by way of example, a substituted or unsubstituted non-aromatic mono or multicyclic ring system of about 3 to about 30 carbon atoms and preferably from 3 to about 6 carbon atoms such as, for example, cyclopropyl, cyclobutyl, cyclopentyl, cyclohexyl, perhydronapththyl, adamantyl and norbornyl groups, bridged cyclic groups or sprirobicyclic groups, e.g., spiro-(4, 4)-non-2-yl and the like, optionally containing one or more heteroatoms, e.g., O and N, and the like.

Representative examples of cycloalkylalkyl groups for use herein include, by way of example, a substituted or unsubstituted cyclic ring-containing radical containing from about 3 to about 30 carbon atoms and preferably from 3 to about 6 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like, wherein the cyclic ring can optionally contain one or more heteroatoms, e.g., O and N, and the like.

Representative examples of cycloalkenyl groups for use herein include, by way of example, a substituted or unsubstituted cyclic ring-containing radical containing from about 3 to about 30 carbon atoms and preferably from 3 to about 6 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 5 to about 30 carbon atoms such as, for example, phenyl, naphthyl, tetrahydronapthyl, indenyl, biphenyl and the like, optionally containing one or more heteroatoms, e.g., O and N, and the like.

Representative examples of arylalkyl groups for use herein include, by way of example, a substituted or unsubstituted aryl group as defined herein directly bonded to an alkyl group as defined herein, e.g., —$CH_2C_6H_5$, —$C_2H_5C_6H_5$ and the like, wherein the aryl group can optionally contain one or more heteroatoms, e.g., O and N, and the like.

Representative examples of a carboxylic acid-containing group for use herein include, by way of example, a carboxylic acid group attached to the rest of the molecule via a linking group, e.g., of the general formula —$R^2C(O)OH$, wherein $R^2$ is a bond, a substituted or unsubstituted alkylene group, a substituted or unsubstituted cycloalkylene, a substituted or unsubstituted cycloalkylalkylene group, a substituted or unsubstituted arylene or a substituted or unsubstituted arylalkylene group as defined herein, e.g., —CH(Ar)(C(O)OH), —C(CH_3)(C(O)OH), and the like.

Representative examples of ester groups for use herein include, by way of example, a carboxylic acid ester having one to 20 carbon atoms and the like.

Representative examples of ether or polyether containing groups for use herein include, by way of example, an alkyl ether, cycloalkyl ether, cycloalkylalkyl ether, cycloalkenyl ether, aryl ether, arylalkyl ether wherein the alkyl, cycloalkyl, cycloalkylalkyl, cycloalkenyl, aryl, and arylalkyl groups are as defined herein. Exemplary ether or polyether-containing groups include, by way of example, alkylene oxides, poly(alkylene oxide)s such as ethylene oxide, propylene oxide, butylene oxide, poly(ethylene oxide)s, poly(ethylene glycol)s, poly(propylene oxide)s, poly(butylene oxide)s and mixtures or copolymers thereof, an ether or polyether group of the general formula —$(R^2OR^3)_t$, wherein $R^2$ has the aforestated meanings, $R^3$ is a substituted or unsubstituted alkyl group, a substituted or unsubstituted cycloalkyl, a substituted or unsubstituted cycloalkylalkyl group, a substituted or unsubstituted aryl or a substituted or unsubstituted arylalkyl group as defined herein and t is at least 1, e.g., —$CH_2CH_2OC_6H_5$ and $CH_2$—$CH_2$—$CH_2$—O—$CH_2$—$(CF_2)_z$—H where z is 1 to 6, —$CH_2CH_2OC_2H_5$, and the like.

Representative examples of alkyl or arylamide groups for use herein include, by way of example, an amide of the general formula —$R^4C(O)NR^5R^6$ wherein $R^4$, $R^5$ and $R^6$ are independently $C_1$-$C_{30}$ hydrocarbons, e.g., $R^4$ can be alkylene groups, arylene groups, cycloalkylene groups and $R^5$ and $R^6$ can be alkyl groups, aryl groups, and cycloalkyl groups as defined herein and the like.

Representative examples of alky or arylamine groups for use herein include, by way of example, an amine of the general formula —$R^7NR^8R^9$ wherein $R^7$ is a $C_2$-$C_{30}$ alkylene, arylene, or cycloalkylene and $R^8$ and $R^9$ are independently $C_1$-$C_{30}$ hydrocarbons such as, for example, alkyl groups, aryl groups, or cycloalkyl groups as defined herein.

Representative examples of heterocyclic ring groups for use herein include, by way of example, a substituted or unsubstituted stable 3 to about 30 membered ring radical, containing carbon atoms and from one to five heteroatoms, e.g., nitrogen, phosphorus, oxygen, sulfur and mixtures thereof. Suitable heterocyclic ring radicals for use herein may be a monocyclic, bicyclic or tricyclic ring system, which may include fused, bridged or spiro ring systems, and the nitrogen, phosphorus, carbon, oxygen or sulfur atoms in the heterocylic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroquinolinyl, tetrahydroisoquinolinyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolidinyl, triazolyl, indanyl, isoxazolyl, iso-oxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, isochromanyl and the like and mixtures thereof.

Representative examples of heteroaryl groups for use herein include, by way of example, a substituted or unsubstituted heterocyclic ring radical as defined herein. The heteroaryl ring radical may be attached to the main structure at any heteroatom or carbon atom that results in the creation of a stable structure.

Representative examples of heteroarylalkyl groups for use herein include, by way of example, a substituted or unsubstituted heteroaryl ring radical as defined herein directly bonded to an alkyl group as defined herein. The heteroarylalkyl radical may be attached to the main structure at any carbon atom from the alkyl group that results in the creation of a stable structure.

Representative examples of heterocyclic groups for use herein include, by way of example, a substituted or unsubstituted heterocylic ring radical as defined herein. The heterocyclic ring radical may be attached to the main structure at any heteroatom or carbon atom that results in the creation of a stable structure.

Representative examples of heterocycloalkyl groups for use herein include, by way of example, a substituted or unsubstituted heterocylic ring radical as defined herein directly bonded to an alkyl group as defined herein. The heterocycloalkyl radical may be attached to the main structure at any carbon atom in the alkyl group that results in the creation of a stable structure.

The substituents in the 'substituted oxygen', 'substituted nitrogen', 'substituted sulfur', 'substituted alkyl', 'substituted alkylene, 'substituted cycloalkyl', 'substituted cycloalkylalkyl', 'substituted cycloalkenyl', 'substituted arylalkyl', 'substituted aryl', 'substituted heterocyclic ring', 'substituted heteroaryl ring,' 'substituted heteroarylalkyl', 'substituted heterocycloalkyl ring', 'substituted cyclic ring' may be the same or different and include one or more substituents such as hydrogen, hydroxy, halogen, carboxyl, cyano, nitro, oxo (=O), thio(=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocycloalkyl ring, substituted or unsubstituted heteroarylalkyl, substituted or unsubstituted heterocyclic ring, and the like.

Generally, the siloxane-containing homopolymer is one that contains at least two [—Si—O—] repeating units in the homopolymer. In one embodiment, the siloxane-containing homopolymer will have from about 2 to about 100 and preferably from about 6 to about 40 [—Si—O—] repeating units in the homopolymer.

One class of siloxane-containing homopolymers is of the general formula:

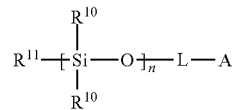

wherein L is a linking group including, by way of example, a bond, a straight or branched $C_1$-$C_{30}$ alkyl group, a $C_1$-$C_{30}$ fluoroalkyl group, a $C_1$-$C_{20}$ ester-containing group, an alkyl ether, cycloalkyl ether cycloalkenyl ether, aryl ether, arylalkyl ether, a polyether containing group, amide-containing group, amine-containing group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkylalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ arylalkyl group, a substituted or unsubstituted $C_5$-$C_{30}$ heteroaryl group, a substituted or unsubstituted $C_3$-$C_{30}$ heterocyclic ring, a substituted or unsubstituted $C_4$-$C_{30}$ heterocyclolalkyl group, a substituted or unsubstituted $C_6$-$C_{30}$ heteroarylalkyl group, a $C_5$-$C_{30}$ fluoroaryl group, or a hydroxyl substituted alkyl ether There is no particular limitation on the organic chemistry used to form the siloxane-containing homopolymer comprising one or more thio carbonyl thio fragments of a RAFT agent and is within the purview of one skilled in the art. Also, the working examples below provide guidance. One example of a method to prepare a siloxane-containing homopolymer is represented below in Scheme I:

SCHEME I

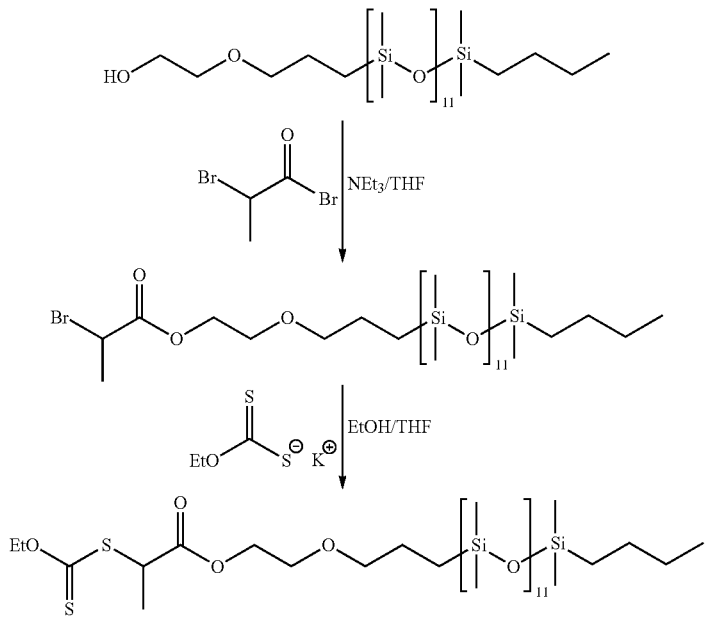

and combinations thereof; $R^{10}$ and $R^{11}$ is independently hydrogen, a straight or branched $C_1$-$C_{30}$ alkyl group, a $C_1$-$C_{30}$ fluoroalkyl group, a $C_1$-$C_{20}$ ester-containing group, an alkyl ether group, cycloalkyl ether group, cycloalkenyl ether group, aryl ether group, arylalkyl ether group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkylalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ arylalkyl group, a substituted or unsubstituted $C_5$-$C_{30}$ heteroaryl group, a substituted or unsubstituted $C_3$-$C_{30}$ heterocyclic ring, a substituted or unsubstituted $C_4$-$C_{30}$ heterocyclolalkyl group, a substituted or unsubstituted $C_6$-$C_{30}$ heteroarylalkyl group, fluorine, a $C_5$-$C_{30}$ fluoroaryl group, a siloxy group such as a trisiloxy group, e.g., trimethylsiloxy, or a hydroxyl group; n is from 2 to 100, and A is independently a thio carbonyl thio fragment as defined herein.

Another class of siloxane-containing homopolymers is of the general formula:

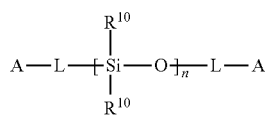

wherein L, A, $R^{10}$ and n have the aforestated meanings.

In addition to the siloxane-containing homopolymer comprising one or more thio carbonyl thio fragments of a RAFT agent, the mixture to be polymerized to form a biomedical device of the present invention include conventional biomedical device-forming or ophthalmic lens-forming monomers. As used herein, the term "monomer" or "monomeric" and like terms denote relatively low molecular weight compounds that are polymerizable by free radical polymerization, as well as higher molecular weight compounds also referred to as "prepolymers", "macromonomers", and related terms. Generally, the biomedical device-forming comonomer contains at least one polymerizable group or free radical polymerizable group. In one embodiment, a suitable comonomer includes hydrophobic monomers, hydrophilic monomers and the like and mixtures thereof.

Representative examples of hydrophilic comonomers include, but are not limited to, unsaturated carboxylic acids, such as methacrylic and acrylic acids; (meth)acrylic substituted alcohols or polyols such as 2-hydroxyethyl methacrylate, 2-hydroxyethyl acrylate, glyceryl methacrylate and the like; vinyl lactams such as N-vinylpyrrolidone and the like; and (meth)acrylamides such as methacrylamide, N,N-dimethylacrylamide and the like and combinations thereof. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art. The hydrophilic monomers can be present in the mixtures in an amount ranging from about 0.1 to about 90 weight percent, based on the total weight of the mixture.

According to various preferred embodiments, the initial mixture to be polymerized can comprise at least one (meth)acrylic substituted alcohol, such as at least one of 2-hydroxyethyl methacrylate and glyceryl methacrylate, preferably in an amount of at least about 0.1 to about 50 weight percent, based on the total weight of the mixture. Preferably, the mixture to be polymerized further includes at least one vinyl lactam, such as N-vinylpyrrolidone and/or at least one (meth)acrylamide, such as N,N-dimethylacrylamide.

Suitable hydrophobic monomers include $C_1$-$C_{20}$ alkyl and $C_3$-$C_{20}$ cycloalkyl (meth)acrylonitriles, fluorinated alkyl methacrylates, long-chain acrylamides such as octyl acrylamide, and the like. The hydrophobic monomers can be present in the mixtures in an amount ranging from about 1 to about 30 weight percent, based on the total weight of the mixture.

Suitable hydrophobic monomers include $C_1$-$C_{20}$ alkyl and $C_3$-$C_{20}$ cycloalkyl (meth)acrylates, substituted and unsubstituted $C_6$-$C_{30}$ aryl (meth)acrylates, (meth)acrylonitriles, fluorinated alkyl methacrylates, long-chain acrylamides such as octyl acrylamide, and the like. The hydrophobic monomers can be present in the mixtures in an amount ranging from about 0.1 weight to about 90 weight percent, based on the total weight of the mixture.

If desired, the mixture to be polymerized may further include a silicone-containing monomer in addition to the siloxane-containing homopolymer comprising one or more thio carbonyl thio fragments of a RAFT agent. In other words, another silicone-containing comonomer which contains from 1 to about 60 silicone atoms, in addition to the siloxane-containing homopolymer comprising one or more thio carbonyl thio fragments of a RAFT agent, may be included in the initial mixture to be polymerized, for example, if it is desired to obtain a copolymer with high oxygen permeability. Any known silicone-containing monomers useful for making biomedical devices such as silicone hydrogels can be used in combination with the siloxane-containing homopolymer to form the biomedical devices such as soft contact lenses of this invention. Applicable silicone-containing monomers are well known in the art and numerous examples are provided in, for example, U.S. Pat. Nos. 4,136,250; 4,153,641; 4,740,533; 5,034,461; 5,070,215; 5,260,000; 5,310,779; and 5,358,995.

Representative examples of applicable silicon-containing monomers include bulky polysiloxanylalkyl(meth)acrylic monomers. An example of a bulky polysiloxanylalkyl(meth) acrylic monomer is represented by the structure of Formula I:

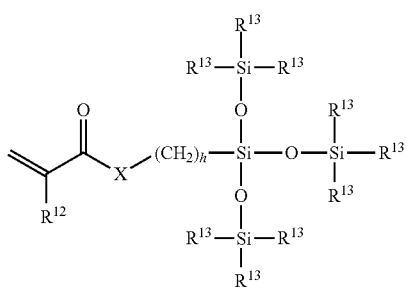

(I)

wherein X denotes —O— or —NR— wherein R denotes hydrogen or a $C_1$-$C_4$ alkyl; $R^{12}$ independently denotes hydrogen or methyl; each $R^{13}$ independently denotes a lower alkyl radical, phenyl radical or a group represented by

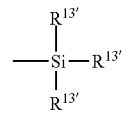

wherein each $R^{13'}$ independently denotes a lower alkyl or phenyl radical; and h is 1 to 10.

Representative examples of other applicable silicon-containing monomers includes, but are not limited to, bulky polysiloxanylalkyl carbamate monomers as generally depicted in Formula Ia:

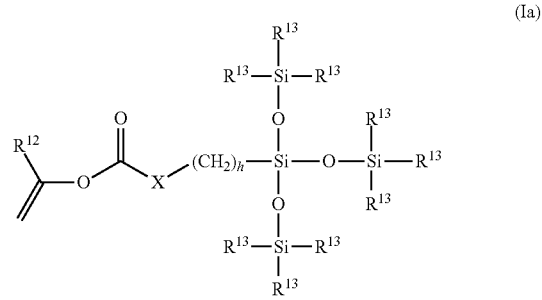

(Ia)

wherein X denotes —NR—; wherein R denotes hydrogen or a $C_1$-$C_4$ alkyl; $R^{12}$ denotes hydrogen or methyl; each $R^{13}$ independently denotes a lower alkyl radical, phenyl radical or a group represented by

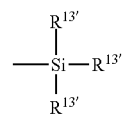

wherein each $R^{13'}$ independently denotes a lower alkyl or phenyl radical; and h is 1 to 10, and the like.

Examples of bulky monomers are 3-methacryloyloxypropyltris(trimethylsiloxy)silane or tris(trimethylsiloxy)silylpropyl methacrylate, sometimes referred to as TRIS and tris(trimethylsiloxy)silylpropyl vinyl carbamate, sometimes referred to as TRIS-VC and the like and mixtures thereof.

Such bulky monomers may be copolymerized with a silicone macromonomer, which is a poly(organosiloxane) capped with an unsaturated group at two or more ends of the molecule. U.S. Pat. No. 4,153,641 discloses, for example, various unsaturated groups such as acryloxy or methacryloxy groups.

Another class of representative silicone-containing monomers includes, but is not limited to, silicone-containing vinyl carbonate or vinyl carbamate monomers such as, for example, 1,3-bis[4-vinyloxycarbonyloxy)but-1-yl]tetramethyldisiloxane; 3-(trimethylsilyl)propyl vinyl carbonate; 3-(vinyloxycarbonylthio)propyl-[tris(trimethylsiloxy)silane]; 3-[tris(trimethylsiloxy)silyl]propyl vinyl carbamate; 3-[tris(trimethylsiloxy)silyl]propyl allyl carbamate; 3-[tris(trimethylsiloxy)silyl]propyl vinyl carbonate; t-butyldimethylsiloxyethyl vinyl carbonate; trimethylsilylethyl vinyl carbonate; trimethylsilylmethyl vinyl carbonate and the like.

Another class of silicon-containing monomers includes polyurethane-polysiloxane macromonomers (also sometimes referred to as prepolymers), which may have hard-soft-hard blocks like traditional urethane elastomers. Examples of silicone urethanes are disclosed in a variety or publications, including Lai, Yu-Chin, "The Role of Bulky Polysiloxanylalkyl Methacrylates in Polyurethane-Polysiloxane Hydrogels," Journal of Applied Polymer Science, Vol. 60, 1193-1199 (1996). PCT Published Application No. WO 96/31792 also discloses examples of such monomers, the contents of which are hereby incorporated by reference in its entirety. Further examples of silicone urethane monomers are represented by Formulae II and III:

$$E(*D*A*D*G)_a*D*A*D*E'; \text{ or} \qquad (II)$$

$$E(*D*G*D*A)_a*D*A*D*E'; \text{ or} \qquad (III)$$

wherein:

D denotes an alkyl diradical, an alkyl cycloalkyl diradical, a cycloalkyl diradical, an aryl diradical or an alkylaryl diradical having 6 to about 30 carbon atoms;

G denotes an alkyl diradical, a cycloalkyl diradical, an alkyl cycloalkyl diradical, an aryl diradical or an alkylaryl diradical having 1 to about 40 carbon atoms and which may contain ether, thio or amine linkages in the main chain;

* denotes a urethane or ureido linkage;

a is at least 1;

A denotes a divalent polymeric radical of Formula IV:

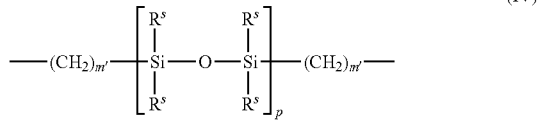

wherein each $R^s$ independently denotes an alkyl or fluoro-substituted alkyl group having 1 to about 10 carbon atoms which may contain ether linkages between the carbon atoms; m' is at least 1; and p is a number that provides a moiety weight of about 400 to about 10,000;

each of E and E' independently denotes a polymerizable unsaturated organic radical represented by Formula V:

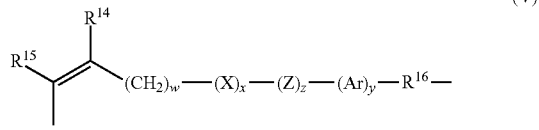

wherein: $R^{14}$ is hydrogen or methyl;

$R^{15}$ is independently hydrogen, an alkyl radical having 1 to 6 carbon atoms, or a —CO—Y—$R^{16}$ radical wherein Y is —O—, —S— or —NH—;

$R^{17}$ is a divalent alkylene radical having 1 to about 10 carbon atoms;

$R^{16}$ is a alkyl radical having 1 to about 12 carbon atoms;

X denotes —CO— or —OCO—;

Z denotes —O— or —NH—;

Ar denotes an aromatic radical having about 6 to about 30 carbon atoms;

w is 0 to 6; x is 0 or 1; y is 0 or 1; and z is 0 or 1.

A preferred silicone-containing urethane monomer is represented by Formula VI:

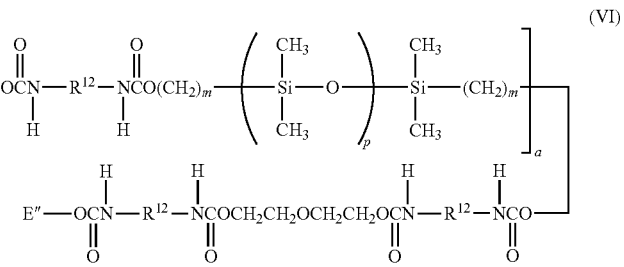

wherein m is at least 1 and is preferably 3 or 4, a is at least 1 and preferably is 1, p is a number which provides a moiety weight of about 400 to about 10,000 and is preferably at least about 30, $R^{12}$ is a diradical of a diisocyanate after removal of the isocyanate group, such as the diradical of isophorone diisocyanate, and each E" is a group represented by:

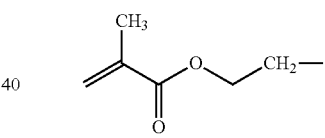

Another class of representative silicone-containing monomers includes fluorinated monomers. Such monomers have been used in the formation of fluorosilicone hydrogels to reduce the accumulation of deposits on contact lenses made therefrom, as described in, for example, U.S. Pat. Nos. 4,954,587; 5,010,141 and 5,079,319. The use of silicone-containing monomers having certain fluorinated side groups, i.e., —(CF$_2$)—H, have been found to improve compatibility between the hydrophilic and silicone-containing monomeric units, see, e.g., U.S. Pat. Nos. 5,321,108 and 5,387,662.

The above silicone materials are merely exemplary, and other materials for use in forming biomedical devices according to the present invention and have been disclosed in various publications and are being continuously developed for use in contact lenses and other biomedical devices can also be used. For example, a biomedical device-forming comonomer can be a cationic monomer such as cationic silicone-containing monomer or cationic fluorinated silicone-containing monomers.

The mixture can also include a crosslinking monomer (a crosslinking monomer being defined as a monomer having multiple polymerizable functionalities). Representative crosslinking monomers include: divinylbenzene, allyl methacrylate, ethyleneglycol dimethacrylate, tetraethyleneglycol dimethacrylate, polyethyleneglycol dimethacrylate, vinyl carbonate derivatives of the glycol dimethacrylates, and methacryloxyethyl vinylcarbonate. When a crosslinking agent is employed, this monomeric material may be included in the mixture at about 0.1 to about 20 weight percent, and more preferably at about 0.2 to about 10 weight percent.

Although not necessarily required, the mixture may also include one or more strengthening agents. Non-limiting examples of suitable strengthening agents are described in U.S. Pat. Nos. 4,327,203; 4,355,147; and 5,270,418; each of which is incorporated herein in its entirety by reference. Specific examples, not intended to be limiting, of such strengthening agents include cycloalkyl acrylates and methacrylates; e.g., tert-butylcyclohexyl methacrylate and isopropylcyclopentyl acrylate.

The mixture to be polymerized may further contain, as necessary and within limits not to impair the purpose and effect of the present invention, various additives such as an antioxidant, coloring agent, ultraviolet absorber, lubricant internal wetting agents, and the like and other constituents as is well known in the art.

The biomedical devices of the present invention, e.g., soft contact lenses or intraocular lenses, can be prepared by polymerizing the foregoing mixtures to form a product that can be subsequently formed into the appropriate shape by, for example, lathing, injection molding, compression molding, cutting and the like. For example, in producing contact lenses, the initial mixture may be polymerized in tubes to provide rod-shaped articles, which are then cut into buttons. The buttons may then be lathed into contact lenses.

Alternately, the biomedical devices such as contact lenses may be cast directly in molds, e.g., polypropylene molds, from the mixtures, e.g., by spincasting and static casting methods. Spincasting methods are disclosed in U.S. Pat. Nos. 3,408,429 and 3,660,545, and static casting methods are disclosed in U.S. Pat. Nos. 4,113,224, 4,197,266, and 5,271,875. Spincasting methods involve charging the mixture to a mold, and spinning the mold in a controlled manner while exposing the mixture to a radiation source such as UV light. Static casting methods involve charging the mixture between two mold sections, one mold section shaped to form the anterior lens surface and the other mold section shaped to form the posterior lens surface, and curing the mixture while retained in the mold assembly to form a lens, for example, by free radical polymerization of the mixture. Examples of free radical reaction techniques to cure the lens material include thermal radiation, infrared radiation, electron beam radiation, gamma radiation, ultraviolet (UV) radiation, and the like; or combinations of such techniques may be used. U.S. Pat. No. 5,271,875 describes a static cast molding method that permits molding of a finished lens in a mold cavity defined by a posterior mold and an anterior mold. As an additional method, U.S. Pat. No. 4,555,732 discloses a process where an excess of a mixture is cured by spincasting in a mold to form a shaped article having an anterior lens surface and a relatively large thickness, and the posterior surface of the cured spincast article is subsequently lathed to provide a contact lens having the desired thickness and posterior lens surface.

Polymerization may be facilitated by exposing the mixture to heat and/or radiation, such as ultraviolet light, visible light, or high energy radiation. A polymerization initiator may be included in the mixture to facilitate the polymerization step. Representative examples of free radical thermal polymerization initiators include organic peroxides such as acetyl peroxide, lauroyl peroxide, decanoyl peroxide, stearoyl peroxide, benzoyl peroxide, tertiarybutyl peroxypivalate, peroxydicarbonate, and the like. Representative UV initiators are those known in the art and include benzoin methyl ether, benzoin ethyl ether, Darocure®1173, 1164, 2273, 1116, 2959, 3331 (EM Industries) and Irgacure® 651 and 184 (Ciba-Geigy), and the like. Generally, the initiator will be employed in the mixture at a concentration of about 0.01 to about 5 percent by weight of the total mixture.

Polymerization is generally performed in a reaction medium, such as, for example, a solution or dispersion using a solvent, e.g., water or an alkanol containing from 1 to 12 carbon atoms such as methanol, ethanol or nonanol. Alternatively, a mixture of any of the above solvents may be used.

Generally, polymerization can be carried out for about 15 minutes to about 72 hours, and under an inert atmosphere of, for example, nitrogen or argon. If desired, the resulting polymerization product can be dried under vacuum, e.g., for about 5 to about 72 hours or left in an aqueous solution prior to use.

Polymerization of the mixtures will yield a polymer, that when hydrated, preferably forms a hydrogel. Generally, the mixture will contain the siloxane-containing homopolymer comprising one or more thio carbonyl thio fragments of a RAFT agent in an amount ranging from about 0.1 to about 40 weight percent, and preferably about 1 to about 20 weight percent, based on the total weight of the mixture. The biomedical device-forming comonomer may be present in the mixture in an amount ranging from about 0.1 to about 90 weight percent, and preferably about 30 to about 80 weight percent, based on the total weight of the mixture.

When producing a hydrogel lens, the mixture may further include at least a diluent that is ultimately replaced with water when the polymerization product is hydrated to form a hydrogel. Generally, the water content of the hydrogel is greater than about 5 weight percent and more commonly between about 10 to about 80 weight percent. The amount of diluent used should be less than about 50 weight percent and in most cases, the diluent content will be less than about 30 weight percent. However, in a particular polymer system, the actual limit will be dictated by the solubility of the various monomers in the diluent. In order to produce an optically clear copolymer, it is important that a phase separation leading to visual opacity does not occur between the comonomers and the diluent, or the diluent and the final copolymer.

Furthermore, the maximum amount of diluent which may be used will depend on the amount of swelling the diluent causes in the final polymers. Excessive swelling will or may cause the copolymer to collapse when the diluent is replaced with water upon hydration. Suitable diluents include, but are not limited to, ethylene glycol; glycerine; liquid poly(ethylene glycol); alcohols; alcohol/water mixtures; ethylene oxide/propylene oxide block copolymers; low molecular weight linear poly(2-hydroxyethyl methacrylate); glycol esters of lactic acid; formamides; ketones; dialkylsulfoxides; butyl carbitol; and the like and mixtures thereof.

If necessary, it may be desirable to remove residual diluent from the lens before edge-finishing operations which can be accomplished by evaporation at or near ambient pressure or under vacuum. An elevated temperature can be employed to shorten the time necessary to evaporate the diluent. The time, temperature and pressure conditions for the solvent removal step will vary depending on such factors as the volatility of the diluent and the specific monomeric components, as can be readily determined by one skilled in the art. If desired, the mixture used to produce the hydrogel lens may further include crosslinking and wetting agents known in the prior art for making hydrogel materials.

In the case of intraocular lenses, the mixtures may further include a monomer for increasing the refractive index of the resultant copolymer. Examples of such monomers are aromatic (meth)acrylates, such as phenyl (meth)acrylate, 2-phenylethyl (meth)acrylate, 2-phenoxyethyl methacrylate, and benzyl (meth) acrylate.

The biomedical devices such as contact lenses obtained herein may be subjected to optional machining operations. For example, the optional machining steps may include buffing or polishing a lens edge and/or surface. Generally, such machining processes may be performed before or after the product is released from a mold part, e.g., the lens is dry released from the mold by employing vacuum tweezers to lift the lens from the mold, after which the lens is transferred by means of mechanical tweezers to a second set of vacuum tweezers and placed against a rotating surface to smooth the surface or edges. The lens may then be turned over in order to machine the other side of the lens.

The lens may then be transferred to individual lens packages containing a buffered saline solution. The saline solution may be added to the package either before or after transfer of the lens. Appropriate packaging designs and materials are known in the art. A plastic package is releasably sealed with a film. Suitable sealing films are known in the art and include foils, polymer films and mixtures thereof. The sealed packages containing the lenses are then sterilized to ensure a sterile product. Suitable sterilization means and conditions are known in the art and include, for example, autoclaving.

As one skilled in the art will readily appreciate other steps may be included in the molding and packaging process described above. Such other steps can include, for example, coating the formed lens, surface treating the lens during formation (e.g., via mold transfer), inspecting the lens, discarding defective lenses, cleaning the mold halves, reusing the mold halves, and the like and combinations thereof.

The following examples are provided to enable one skilled in the art to practice the invention and are merely illustrative of the invention. The examples should not be read as limiting the scope of the invention as defined in the claims.

In the following examples, S,S'-bis(α,α'-dimethyl-α"-acetic acid)trithiocarbonate (1) and S-1-dodecyl-S'-(α,α'-dimethyl-α"-acetic acid)-trithiocarbonate (2) is used as a source of a trithiocarbonyl group. Both chain transfer agents were synthesized according to the one-pot synthesis reported by Lai et al., *Macromolecules*, 35, 6754 (2002). Symmetrical structure of (1) is suitable for the synthesis of a multifunctional polydimethylsiloxane (PDMS) RAFT macromonomer whereas chain transfer agent (2) is suitable for the synthesis of a mono and difunctional PDMS RAFT homopolymer.

In the examples, the following abbreviations are used.
DMA: N,N-dimethylacrylamide
HEMA: 2-hydroxyethyl methacrylate
NVP: N-vinyl-2-pyrrolidone
THF: tetrahydrofuran
TRIS-MA: tris(trimethylsiloxy)silylpropyl methacrylate
TRIS-VC: tris(trimethylsiloxy)silylpropyl vinyl carbamate
D1173: 2-hydroxy-2-methyl-1-phenylpropan-1-one (available as Darocur® 1173 initiator)
Vinal Acid: Vinylcarbamate of β-Alanine having the structure

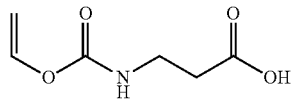

V2D25: Divinylcarbonate of PDMS diol having the structure

Ma2D37: Dimethacrylamide of a PDMS diamine having the structure

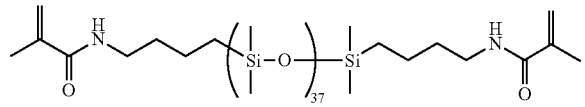

MCR-C12: is a monohydroxyethoxypropyl terminated polydimethylsiloxane having the structure:

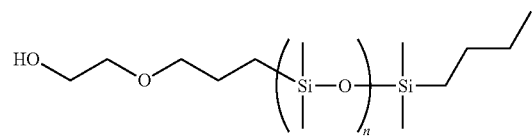

wherein n is an average of 12.

Example 1

Preparation of Multifunctional Ester-Based PDMS RAFT Homopolymer (4)

Oxalyl chloride (5.0 mL, mmol) was added while stirring to S,S'-bis(α,α'-dimethyl-α"-acetic acid)trithiocarbonate 1 (1.0 g, 3.6 mmoL) kept under nitrogen at room temperature. At the end of the addition, the resulting heterogeneous mixture was warmed up to 60° C. for 3 hours, resulting in the formation of a bright yellow solution. The excess oxalyl chloride was evaporated under reduced pressure to yield 1.05 g of S,S'-bis(α,α'-dimethyl-α"-acetyl chloride)trithiocarbonate as a white solid.

Acetyl chloride was dissolved in dry methylene chloride (50 mL) and added dropwise into a solution of hydroxylpropyl terminated PDMS diol (6.77 g, 3.22 mmol) in 200 mL of anhydrous methylene chloride with vigorous stirring at 0° C. After the reaction mixture was stirred for 24 hours at room temperature, the solvent was removed under reduced pressure to give 6.59 g of yellow viscous oil, which was eluted through a short silica gel column using hexane to yield pure multifunctional ester-based PDMS macro RAFT agent (4) (4.90 g). The reaction to provide the multifunctional ester-based PDMS RAFT homopolymer (4) of this example is generally shown below in Scheme II.

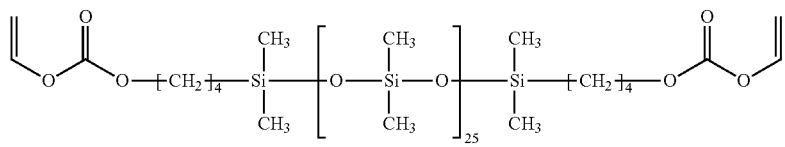

SCHEME II

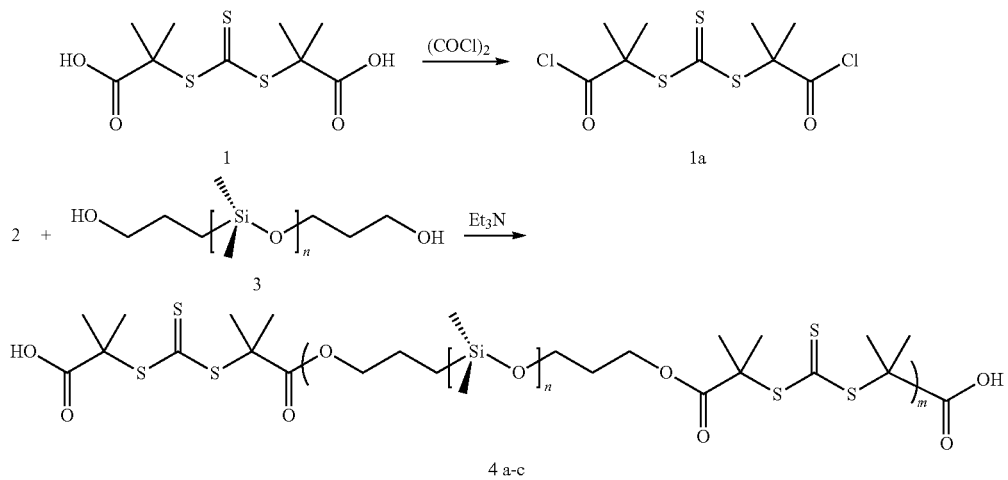

wherein n is an average of 25 and m is an average of 10.

Example 2

Preparation of Multifunctional Amide-Based PDMS RAFT Homopolymer (6)

In a three-neck round bottom flask 8.52 g (3.4 mmoL) of PDMS precursor was dissolved in methylene chloride (150 mL). Triethylamine (1.43 g, 14.2 mmoL) was added, and the solution was cooled in an ice-water bath. In the meantime, oxalyl chloride (6 mL) was added to another one-neck round bottom flask containing 1.0 g (3.6 mmoL) of trithiocarbonate diacid (1). After stirring at 60° C. for 2 hours, the excess oxalyl chloride is evaporated under reduced pressure. The remains were dissolved in 50 mL dry methylene chloride and added dropwise to the PDMS diamine solution with vigorous stirring. The reaction mixture was stirred for 18 hour at room temperature. The solvent was removed by vacuum and the yellow oil obtained was filtered through short plug of silica-gel (eluens: $CH_2Cl_2$/MeOH 3:1). Evaporation of the combined fractions afforded 7.92 g of multifunctional amide-based PDMS RAFT macromonomer (6). The reaction to provide the multifunctional ester-based PDMS RAFT homopolymer (6) of this example is generally shown below in Scheme III.

Example 3

Preparation of Difunctional Ester-Based PDMS RAFT Homopolymer (9)

Oxalyl chloride was added to RAFT-CTA (2) (2.05 g, 5.6 mmoL) at room temperature with rapid stirring, and under a nitrogen atmosphere. After 4 hours of stirring, the evolution of gases had ceased and the reaction was homogenous. The excess oxalyl chloride was removed under reduced pressure to yield acyl chloride (10) (2.1 g), which was dissolved in 20 mL of anhydrous methylene chloride. This solution was gradually added dropwise into a solution of PDMS diol 3 (4.48 g, 2.2 mmoL) in 80 mL of anhydrous methylene chloride. The reaction mixture was stirred for 14 hours at room temperature. At the end of the reaction, methanol (2 mL) was added to quench the remaining acyl chloride. The solvents were removed under reduced pressure to give 6.50 g of reddish oil, which was eluted through a silica gel column using methylene chloride/hexane (gradient elution 5'→50 v/v % $CHCl_2$/hexane) as eluent to separate the difunctional macro RAFT agent (4.5 g) from the monofunctional RAFT agent (0.6 g) obtained as a byproduct, as well as unreacted starting diacid. The reaction to provide the difunctional ester-based PDMS RAFT homopolymer (9) of this example is generally shown below in Scheme IV.

SCHEME III

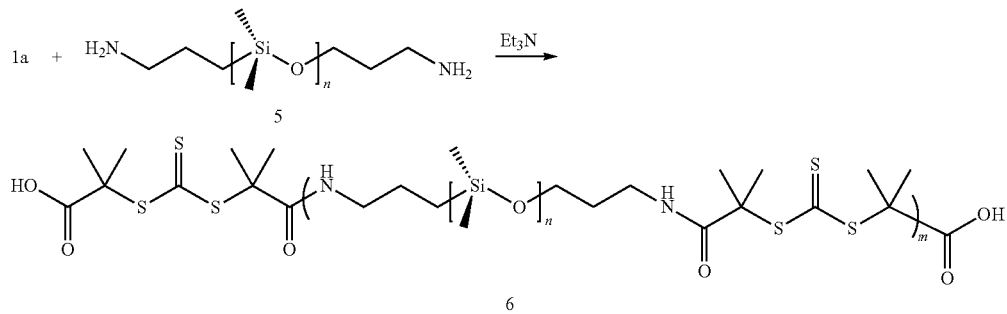

wherein n is an average of 25 and m is an average of 10.

SCHEME IV

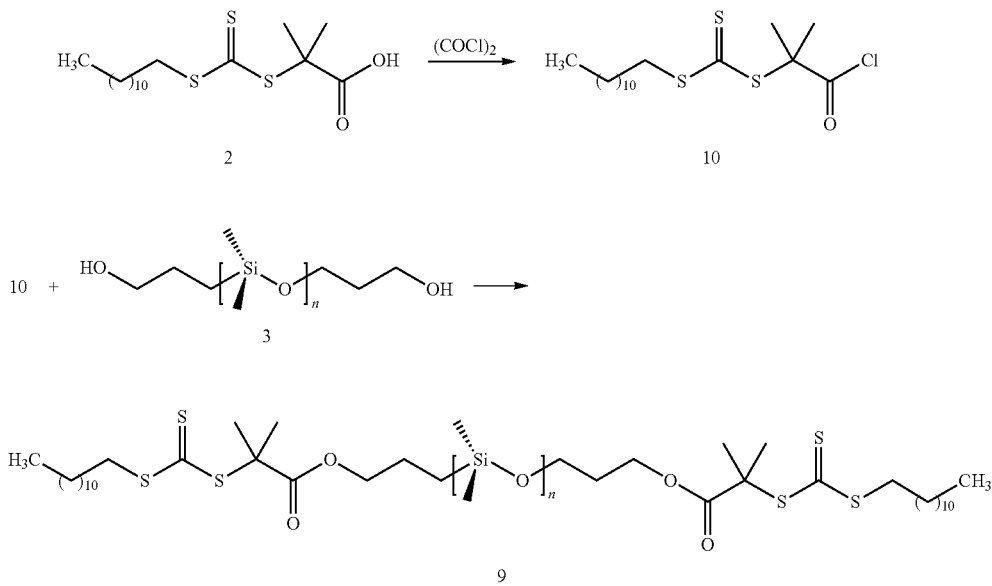

wherein n is an average of 25.

Example 4

Preparation of a Difunctional Amide-Based PDMS RAFT Homopolymer (5)

The amide-based PDMS RAFT agent (5) was synthesized in substantially the same manner as the ester-based macro RAFT agent (9) in Example 3. Flash chromatography of the crude reaction mixture on silica gel using hexane/CHCl$_2$ as eluent (gradient elution 50-100 v/v % hexane/CHCl$_2$) afforded the difunctional amide-based PDMS RAFT macromonomer (5) in 80% isolated yield. The reaction to provide the difunctional amide-based PDMS RAFT homopolymer (5) of this example is generally shown below in Scheme V.

followed by dropwise addition of bromo-i-propionylbromide (3.18 mL, 30 mmoL). The solution was then left overnight at room temperature. The resulting solution was filtered and solvent was removed under reduced pressure. The resulting yellow oil obtained was dissolved in methylene chloride (150 mL), and subsequently washed with saturated sodium hydrogencarbonate solution (2×100 mL). The organic layer was dried over anhydrous magnesium sulfate, filtered, and the solvent was removed under reduced pressure to give the desired product as yellow viscous oil. Yield: 22.3 g.

Next, PDMS di-isopropylbromide (4 g, 1.44 mmoL) was dissolved in ethanol (5 mL). Potassium xanthate (1.0 g, 6.24 mmoL) was added to the stirred solution, and the solution was gently refluxed at 60° C. overnight. The reaction mixture was

SCHEME V

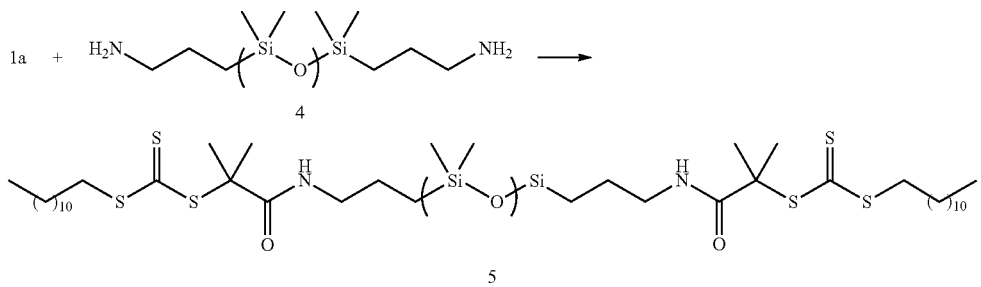

Example 5

Preparation of Xanthate-PDMS-Xantate RAFT Homopolymer (9)

Hydroxypropyl-terminated PDMS (20 g, 10 mmoL) was dissolved in anhydrous tetrahydrofurane (200 mL). Triethylamine (5.58 mL, 40 mmoL) was added to the stirred solution quenched by adding water followed by extraction with methylene chloride. After evaporation of solvent, the residue was chromatographed on silica-gel using hexane/methylene chloride mixture (0-50% v/v) as an eluent to give 1.82 g of pure dixanthate. The combined pure fractions were analyzed by GPC analysis and NMR spectroscopy. The reaction to provide the xanthate-PDMS-xantate RAFT homopolymer (9) of this example is generally shown below in Scheme VI.

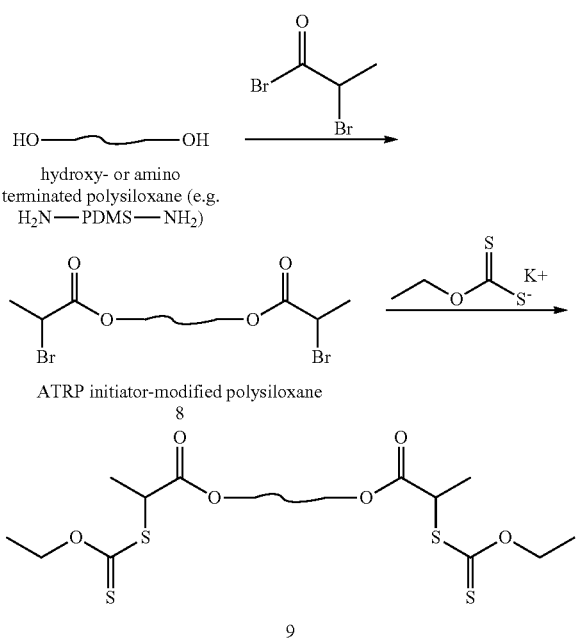

Example 6

Preparation of Xanthate-PDMS RAFT Homopolymer

To a flame dried 500 mL 3-neck round bottom flask equipped with a nitrogen inlet, magnetic stir bar, 0° C. ice water bath, and a Friedrich's condenser were added 30.12 g of MCR-C12 (0.026 moles), 5.88 g of triethylamine (0.0581 moles) and 200 mL THF while stirring at 0° C. 9.48 g of bromo-1-propionylbromide (0.0439 moles) and 50 mL THF were added dropwise through an addition funnel over a period of one hour. The reaction was allowed to proceed overnight (16-18 hrs) while equilibrating to room temperature. The salts were filtered off and 10 mL deionized water in 30 mL THF was added and allowed to stir for 30 minutes. The solvents were removed under pressure. An additional 100 mL of toluene was added and solvent plus residual water was removed under reduced pressure. 25 mL hexane was added and the solution ran through silica column (200 g) and 2-bromoproprionate MCR-C12 was isolated on the rotary evaporator (25.19 gm; 76% yield). The product was confirmed using 1H-NMR.

Next, to a 250 mL round bottom flask equipped with a nitrogen inlet, magnetic stirrer, Friedrich's condenser, and 0° C. ice water bath was added 10.02 g of 2-bromoproprionate MCR-C12 (7.82×10-3 moles) with 25 mL EtOH:THF and allowed to stir in the ice water bath. Once 0° C. was achieved, 1.51 g of potassium ethyl xanthogenate ($9.38 \times 10^{-3}$ moles) was added slowly using a funnel and rinsed with an additional 25 mL EtOH:THF. The reaction was allowed to proceed for 18 hours acclimating to room temperature on its own. 100 mL deionized water was added to the reaction flask. The contents of the flask were extracted 4 times with 100 mL hexanes retaining the organic layers. The organic layers were combined and dried over anhydrous sodium sulfate, filtered, and solvent was removed under reduced pressure to obtain MCR-C12-(ethyl xanthyl proprionate). (8.31 grams; 81% yield). The product structure was confirmed using 1H-NMR. The reaction to provide the xanthate-PDMS RAFT homopolymer of this example is generally shown below in Scheme VII.

SCHEME VII

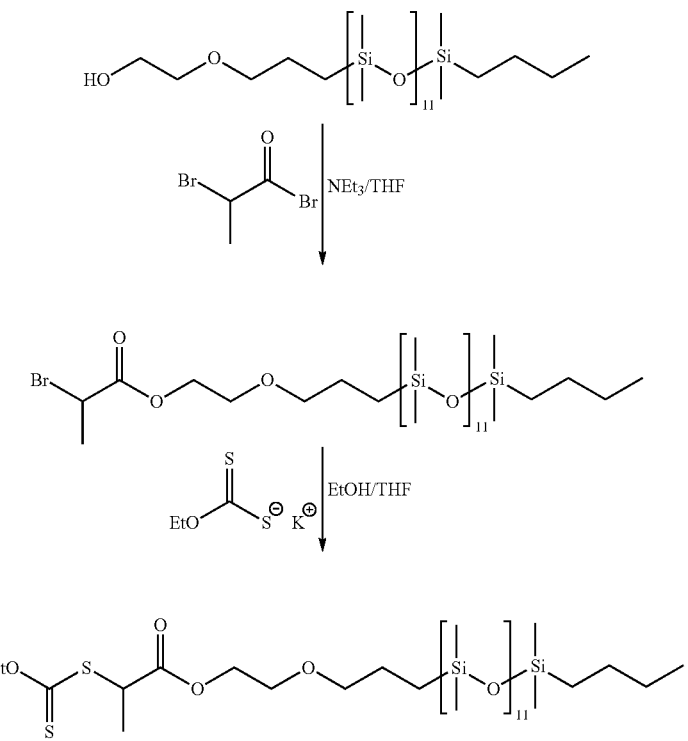

Example 7

Preparation of Monofunctional Ester-Based PDMS RAFT Homopolymer (13)

13 mL of oxalyl chloride was added to RAFT-CTA (2) (3.33 g, 8.2 mmoL) at room temperature with rapid stirring, and under a nitrogen atmosphere. After 4 hours of stirring, the evolution of gases had ceased and the reaction was homogenous. The excess oxalyl chloride was removed under reduced pressure to yield acyl chloride (10) (3.4 g) which was dissolved in 20 mL of anhydrous methylene chloride. This solution was gradually added dropwise into a solution of MCR-C12 (7.67 g, 7.2 mmoL) in 50 mL of anhydrous methylene chloride. The reaction mixture was stirred for 14 hours at room temperature. At the end of the reaction, methanol (2 mL) was added to quench the remaining acyl chloride. The reaction mixture was then transferred to a 500 mL separatory funnel and extracted with 2×50 mL 0.1N HCL wash, 2×50 mL sodium bicarbonate, and 1×50 mL brine solution. The dichloromethane was removed under reduced pressure and the residue was redissolved in hexane and eluted through a short plug of silica gel column using ethyl acetate/hexane (5/95 v/v % EA/hexane). The product was confirmed by NMR and MALDI. The reaction to provide the monofunctional ester-based PDMS RAFT homopolymer (13) of this example is generally shown below in Scheme VIII.

SCHEME VIII

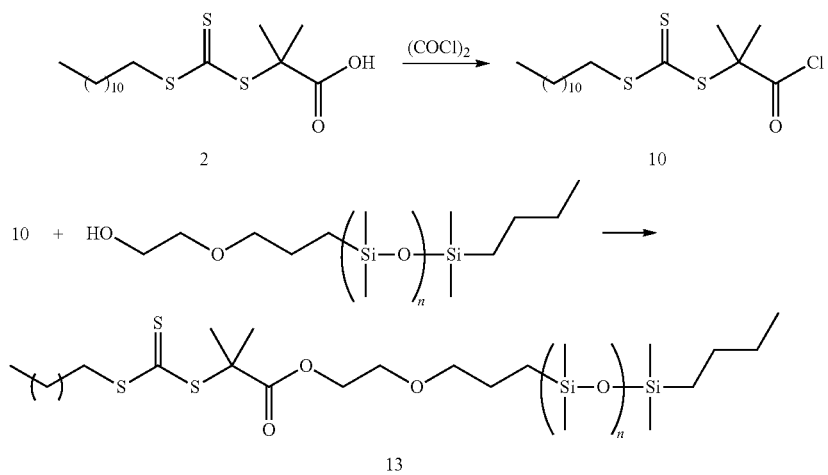

A mixture of each of the formulations in Table 1 was cast in a polypropylene contact lens mold. All mold parts were placed in a nitrogen chamber at least 18 hours prior to casting. In the casting procedure, the anterior mold was filled with the specified volume of the mixture and then capped with a posterior mold half under nitrogen. The molds were placed in a holding plate and transferred to a nitrogen purged oven where they were cured by exposure to UV light under a continuous nitrogen purge for 1-18 hours at ambient temperature or 55° C. The molds were separated manually and the lenses were released in a 30% solution of isopropyl alcohol/water overnight. The lenses were extracted by swelling in 100% isopropyl alcohol for four hours. The isopropyl alcohol concentration was reduced to 50% with water and then the lenses were stepped into 100% water.

Comparative Example A and Examples 8-10

Preparation of Contact Lenses

Contact lenses were prepared using the difunctional ester-based PDMS RAFT homopolymer (9) of Example 3. The amounts and ingredients for each of the formulations of Comparative Example A and Examples 8-10 are set forth below in Table 1. The amounts listed in Table 1 are in parts by weight.

TABLE 1

| Ingredients | Comp. Ex. A | Ex. 8 | Ex. 9 | Ex. 10 |
|---|---|---|---|---|
| Ma2D37 | 15.0 | 12.5 | 10.0 | 10.0 |
| TRIS | 40.0 | 40.0 | 40.0 | 40.0 |
| NVP | 35.0 | 35.0 | 35.0 | 35.0 |
| DMA | 5.0 | 5.0 | 5.0 | 5.0 |
| HEMA | 5.0 | 5.0 | 5.0 | 5.0 |
| RAFT homopolymer (9) (Ex. 3) | 0.0 | 5.0 | 5.0 | 10.0 |
| Hexanol | 5.0 | 5.0 | 5.0 | 5.0 |
| D1173 | 0.5 | 0.5 | 0.5 | 0.5 |
| Total | 105.5 | 108.0 | 105.5 | 110.5 |

Comparative Example B and Examples 11-13

Preparation of Contact Lenses

Contact lenses were prepared using the xanthate-PDMS-xantate RAH homopolymer (9) of Example 5. The amounts and ingredients for each of the formulations of Comparative Example B and Examples 11-13 are set forth below in Table 2. The amounts listed in Table 2 are in parts by weight.

TABLE 2

| Ingredients | Comp. Ex. B | Ex. 11 | Ex. 12 | Ex. 13 |
|---|---|---|---|---|
| V2D25 | 15.0 | 12.5 | 10.0 | 10.0 |
| TRIS-VC | 55.0 | 55.0 | 55.0 | 55.0 |
| NVP | 30.0 | 30.0 | 30.0 | 30.0 |

TABLE 2-continued

| Ingredients | Comp. Ex. B | Ex. 11 | Ex. 12 | Ex. 13 |
| --- | --- | --- | --- | --- |
| Vinal Acid | 1.0 | 1.0 | 1.0 | 1.0 |
| RAFT homopolymer (9) (Ex. 5) | 0.0 | 5.0 | 5.0 | 10.0 |
| Nonanol | 15.0 | 15.0 | 15.0 | 15.0 |
| D1173 | 0.5 | 0.5 | 0.5 | 0.5 |
| Total | 105.5 | 108.0 | 105.5 | 110.5 |

A mixture of each of the formulations in Table 2 was cast in a polypropylene contact lens mold. All mold parts were placed in a nitrogen chamber at least 18 hours prior to casting. In the casting procedure, the anterior mold was filled with the specified volume of the mixture and then capped with a posterior mold half under nitrogen. The molds were placed in a holding plate and transferred to a nitrogen purged oven where they were cured by exposure to UV light under a continuous nitrogen purge for 1-18 hours at ambient temperature or 55° C. The molds were separated manually and the lenses were released in a 30% solution of isopropyl alcohol/water overnight. The lenses were extracted by swelling in 100% isopropyl alcohol for four hours. The isopropyl alcohol concentration was reduced to 50% with water and then the lenses were stepped into 100% water.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A biomedical device comprising a polymerization product of a mixture comprising (a) a siloxane-containing homopolymer which has only one thio carbonyl thio fragment of a reversible addition fragmentation chain transfer (RAFT) agent; and (b) one or more biomedical device-forming comonomers.

2. The biomedical device of claim 1, wherein the thio carbonyl thio fragment is selected from the group consisting of dithioester fragment, xanthate fragment, dithiocarbamate fragment and trithiocarbonate fragment.

3. The biomedical device of claim 1, wherein the siloxane-containing homopolymer is endcapped with the thio carbonyl fragment of the RAFT agent.

4. The biomedical device of claim 1, wherein the biomedical device-forming comonomer is a siloxane-containing monomer.

5. The biomedical device of claim 4, wherein the mixture further comprises a hydrophilic monomer, hydrophobic monomer or both.

6. The biomedical device of claim 1, wherein the biomedical device-forming comonomer is a hydrophilic monomer or hydrophobic monomer.

7. The biomedical device of claim 1, wherein the biomedical device-forming comonomer is a hydrophilic monomer selected from the group consisting of an unsaturated carboxylic acid, acrylamide, vinyl lactam, poly(alkyleneoxy)(meth)acrylate, (meth)acrylic acid, hydroxyl-containing-(meth)acrylate, hydrophilic vinyl carbonate, hydrophilic vinyl carbamate monomer, hydrophilic oxazolone monomer, and mixtures thereof.

8. The biomedical device of claim 1, wherein the biomedical device-forming comonomer is a hydrophilic monomer selected from the group consisting of methacrylic acid, acrylic acid, 2-hydroxyethylmethacrylate, 2-hydroxyethylacrylate, N-vinyl pyrrolidone, N-vinyl caprolactone, methacrylamide, N,N-dimethylacrylamide, ethylene glycol dimethacrylate and mixtures thereof.

9. The biomedical device of claim 1, wherein the siloxane-containing homopolymer comprises about 0.1 to about 40 weight percent of the mixture and the biomedical device-forming comonomer comprises about 0.1 to about 90 weight percent of the mixture.

10. The biomedical device of claim 1, wherein the mixture further comprises (c) a crosslinking agent.

11. The biomedical device of claim 1, wherein the device is a contact lens.

12. The biomedical device of claim 11, wherein the contact lens is a rigid gas permeable contact lens.

13. The biomedical device of claim 11, wherein the contact lens is a soft contact lens.

14. The biomedical device of claim 11, wherein the contact lens is a hydrogel contact lens.

15. The biomedical device of claim 1, wherein the device is an intraocular lens.

16. The biomedical device of claim 1, wherein the device is a corneal implant.

17. A silicone hydrogel which is a hydrated polymerization product of a mixture comprising (a) a siloxane-containing homopolymer which has only one thio carbonyl thio fragment of a reversible addition fragmentation chain transfer (RAFT) agent; and (b) a hydrophilic comonomer.

\* \* \* \* \*